United States Patent [19]

Remy

[11] 4,031,222

[45] June 21, 1977

[54] TRIFLUOROMETHYLTHIO (AND SULFONYL) DERIVATIVES OF CYPROHEPTADINE ANALOGS

[75] Inventor: David C. Remy, North Wales, Pa.

[73] Assignee: Merck & Co., Inc., Rahway, N.J.

[22] Filed: Dec. 22, 1975

[21] Appl. No.: 642,863

[52] U.S. Cl. .......................... 424/267; 260/293.62
[51] Int. Cl.² ........................................ C07D 211/70
[58] Field of Search ............... 260/293.62; 424/267

[56] References Cited

UNITED STATES PATENTS 3,851,059  11/1974  Prugh ............................... 424/267

FOREIGN PATENTS OR APPLICATIONS 3,558M  9/1965  France

OTHER PUBLICATIONS

Ebnother et al., Helv. Chim. Acta 48, 1237 (1965).

*Primary Examiner*—Cecilia M. S. Jaisle
*Attorney, Agent, or Firm*—William H. Nicholson; Harry E. Westlake, Jr.

[57] ABSTRACT

Cyproheptadine derivatives substituted with a trifluoromethylthio or trifluoromethylsulfonyl group in one of the benzo rings and having a hydroxyalkyl or cycloalkylalkyl group on the piperidine nitrogen are potent antipsychotic agents, with a low propensity to induce extrapyramidal side effects that are experienced with most major tranquilizers. The tranquilizing activity is predominantly in the levorotatory enantiomers, whereas the dextrorotatory enantiomers have anticholinergic activity. Each enantiomer is useful as a source of the other by racemization. The novel compounds are prepared by treatment of the corresponding iodo or bromo compound with bis(trifluoromethylthio)mercury and copper powder.

15 Claims, No Drawings

TRIFLUOROMETHYLTHIO (AND SULFONYL) DERIVATIVES OF CYPROHEPTADINE ANALOGS

BACKGROUND OF THE INVENTION

Traditionally, in the dibenzocycloheptene series of compounds, those with a piperidinylidene group in the 5-position have been considered to be without notable antipsychotic action. Recently, however, 3-cyanocyproheptadine, and particularly the levorotatory enantiomer thereof was found to have antipsychotic activity.

Surprisingly, it has now been found that trifluoromethylthio and trifluoromethylsulfonyl derivatives of cyproheptadine carrying a hydroxyalkyl or cycloalkylalkyl group on the piperidine nitrogen are also potent antipsychotic agents, with a low propensity to induce extrapyramidal side effects.

The antipsychotic activity resides predominantly in the levorotatory enantiomers, whereas the dextrorotatory enantiomers, although lacking in antipsychotic activity, are anticholinergic agents. Each enantiomer is additionally useful as a source of the other by a process of racemization.

It is thus an object of the present invention to provide novel compounds which are potent antipsychotic agents with a very low propensity to induce the extrapyramidal side effects experienced with most major tranquilizers, and to provide novel compounds with anticholinergic activity.

It is a further object of this invention to provide novel processes for the preparation of the novel compounds.

Another object of the invention is to provide novel pharmaceutical compositions comprising the novel compounds as active ingredient.

Another object of the invention is to provide a novel method of treating psychoses by administration of the novel antipsychotic compounds or pharmaceutical compositions thereof to a patient.

Another object of this invention is to provide novel intermediates from which the pharmacologically active compounds are prepared

DETAILED DESCRIPTION OF THE INVENTION

The novel compounds of this invention have the following structural formula:

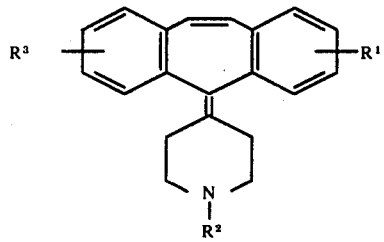

or pharmaceutically acceptable salt thereof, wherein:
$R^1$ represents $-SCF_3$ or $-SO_2CF_3$;
$R^2$ represents (1) 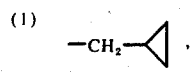

(2) 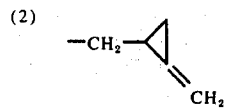

(3) 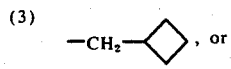, or (4) $-CH_2CH_2OH$;

and
$R^3$ represents hydrogen, lower alkyl of 1–3 carbon atoms, or fluoro.

A preferred embodiment of the novel compounds is that wherein $R^3$ is hydrogen

An even more preferred embodiment of the novel compounds is that wherein $R^3$ is hydrogen, and $R^1$ is $-SCF_3$.

A still more preferred embodiment is that wherein $R^3$ is hydrogen, $R^1$ is $-SCF_3$ in the 3-position, and $R^2$ is

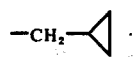

The novel compounds of this invention, and the preferred embodiments thereof, exist as (−), or levorotatory enantiomers, and as (+), or dextrorotatory enantiomers, and mixtures thereof. Included within the scope of this invention are the levo- and dextrorotory enantiomers and any mixtures thereof including the racemic mixtures.

A more preferred aspect of the novel compounds and the preferred embodiments thereof is the (−), or levorotatory enantiomer.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the precipitated salt or evaporation of the solvent.

Another embodiment of this invention is the compound of structural formula:

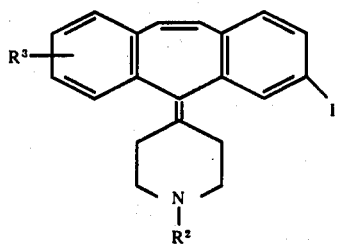

wherein $R^2$ and $R^3$ are as previously defined. Preferred aspects of the present embodiment are the levorotatory and dextrorotatory enantiomers thereof. These compounds are useful as starting materials for the pharmacologically active novel compounds of this invention.

The introduction of nuclear substituents into aromatic rings of cyproheptadine derivatives and analogs results not only in significant changes in the biological spectra of these compounds, but also results in the introduction of optical isomerism. Optical isomerism due to restricted rotation is known as atropisomerism. The resulting enantiomers or optical isomers are also known as atropisomers. (Ebnother et al., *Helv. Chim. Acta*, 48, 1237–1249 (1965)) In the case of cyproheptadine derivatives and analogs that are unsymmetrically substituted, such as the 3-substituted analogs and derivatives, atropisomerism results from the non-bonded interactions between the aromatic protons in the 4- and 6-positions and the allylic protons of the piperidine ring. These non-bonded interactions restrict the inversion of the 7-membered ring in the cyproheptadine derivatives and analogs thus leading to atropisomerism. In the case of these cyproheptadine analogs and derivatives, the free energy barriers to inversion are sufficiently high to allow the isolation and characterization of the atropisomers.

An important novel process for preparing certain of the novel compounds of this invention comprises introduction of the trifluromethylthio group by treating the corresponding iodo or bromo compound with an excess of bis(trifluoromethylthio)mercury and copper powder in an inert organic solvent such as dimethylformamide, hexamethylphosphoramide, or the like at 50 to about 200° C. for 2 to about 24 hours.

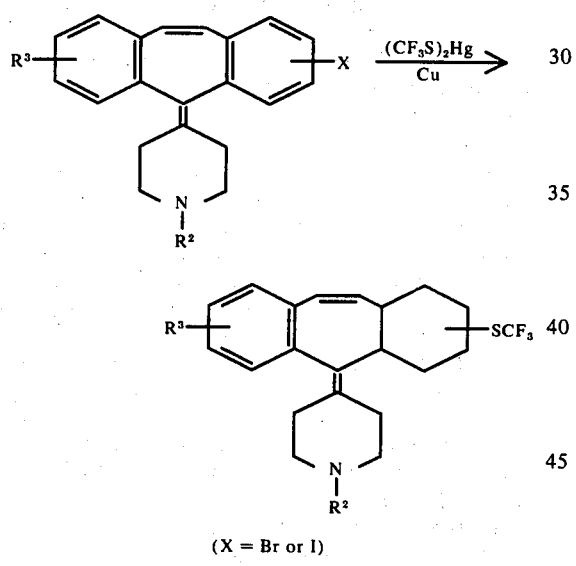

(X = Br or I)

However, temperatures above about 100° C. and times of reaction longer than about 12 hours are not advisable if the starting material is enriched in one or the other optical isomers, inasmuch as high temperatures can cause racemization thus reducing the isomer purity of the product. If optical purity of the product is not important, temperatures as high as 200° C. and times as long as about 24 hours are not unreasonable. In the previous chemical equation where X is Br, temperatures above 150° C. are recommended.

In the foregoing description, the reagents are indicated to be bis-(trifluoromethylthio)mercury and copper. However, the reagent responsible for introduction of the trifluoromethylthio group in the novel process is in fact trifluoromethylthiocopper formed in situ from the above-named reagents.

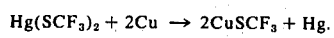

Another useful process for obtaining some of the novel compounds of this invention is shown schematically as follows:

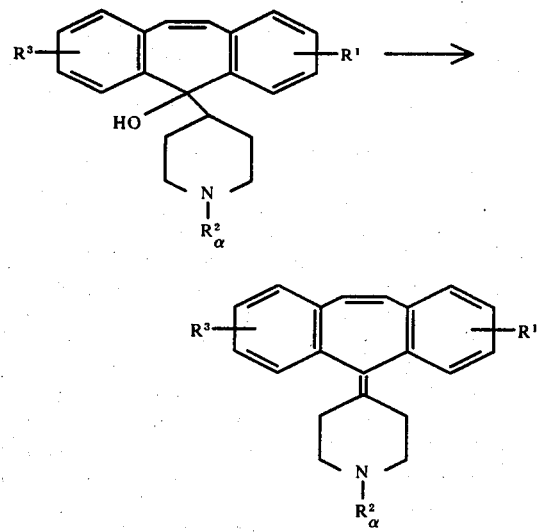

where $R^2_\alpha$ is

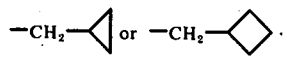

This process comprises heating the starting material with a dehydrating agent such as hydrochloric acid or a mixture of trifluoroacetic acid and trifluoroacetic anhydride, preferably the latter at about 50° C. to reflux temperature for 10 to about 100 hours.

A third process for obtaining racemates of the novel compounds of this invention comprises alkylation of the piperidine nitrogen and is shown as follows:

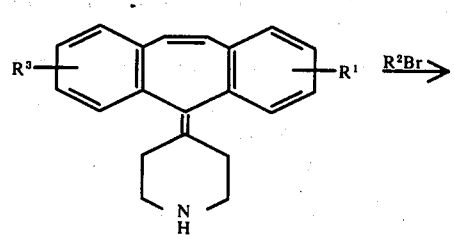

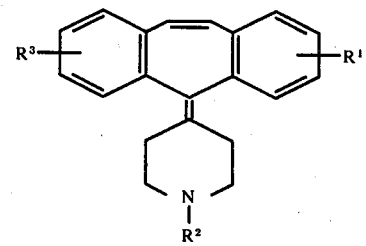

The process comprises treating the secondary amine starting material with an excess of the reagent $R^2Br$ in an inert organic solvent such as a lower alkanol, preferably ethanol, in the presence of an acid acceptor such as a basic resin, pyridine, quinoline, or a solid alkali metal bicarbonate such as sodium bicarbonate, and heating the mixture at 50° C. to reflux temperature from 12 to about 48 hours.

In the case wherein $R^2$ is $-CH_2CH_2OH$, the preferred reagent to employ is ethylene oxide. The process is conducted by treating the secondary amine starting material with an excess of ethylene oxide in a lower alkanol such as methanol or ethanol at about −80° C. and permitting the reaction mixture to warm spontaneously to room temperature and maintaining at room temperature about 10 to 24 hours.

A fourth process of this invention is useful for obtaining the enantiomers of the novel iodo intermediates of this invention and comprises resolution of the racemic iodo starting materials. This process involves forming diastereomeric salts of a mixture of the desired enantiomers with one enantiomer of an optically active acid such as di-(p-toluoyl)tartaric acid, or malic acid, or the like, in a suitable solvent such as a lower alkanol, such as methanol, ethanol, propanol, or benzene, acetonitrile, nitromethane, acetone, or the like, and isolating by crystallization the less soluble diastereomeric salt. The isolated diastereomeric salt, if desired, may be then recrystallized until further recrystallization fails to change the degree of optical rotation. The desired optically active product as the free base is then obtained by treating the diastereomeric salt thereof with a base.

The other enantiomer is obtained from the mother liquors obtained above by crystallization of the diastereomeric salt therefrom, and if desired, repeated recrystallization to constant optical rotation, followed by liberation of the optically active free base.

Alternatively, the contents of the above described mother liquors are concentrated to dryness, the residue is treated with a base to liberate the optically impure free base. This is then treated with the optical antipode of the previously employed optically active acid to form the diastereomeric salt. If desired, this salt may be then purified by repeated recrystallization to constant optical rotation. The free base of the desired compound is then liberated from the diasteriomeric salt by treatment with a base.

Any of the optically enriched free base products obtained as described above can be racemized by heating a solution of the product in an inert solvent until a sample fails to show optical activity. It is convenient to reflux a toluene solution for about 10–30 hours. In this manner, additional quantities of the racemates can be obtained.

The starting materials required for practicing the novel processes of this invention are either known in the prior art or are readily obtained by one or more of the processes outlined below. Details for the illustrated chemical transformations are provided in the Examples.

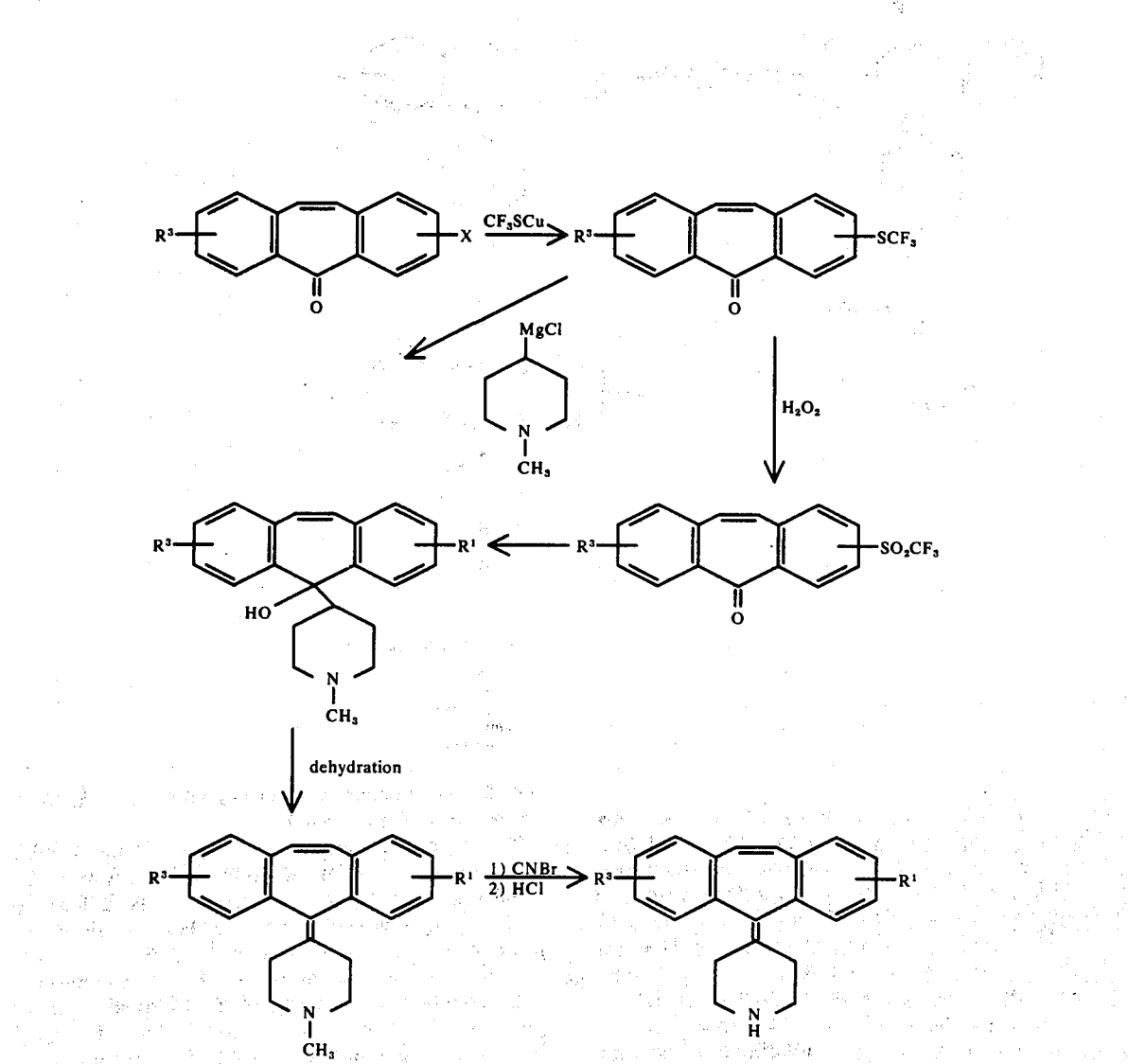

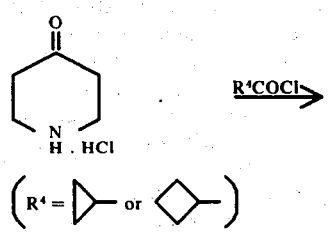
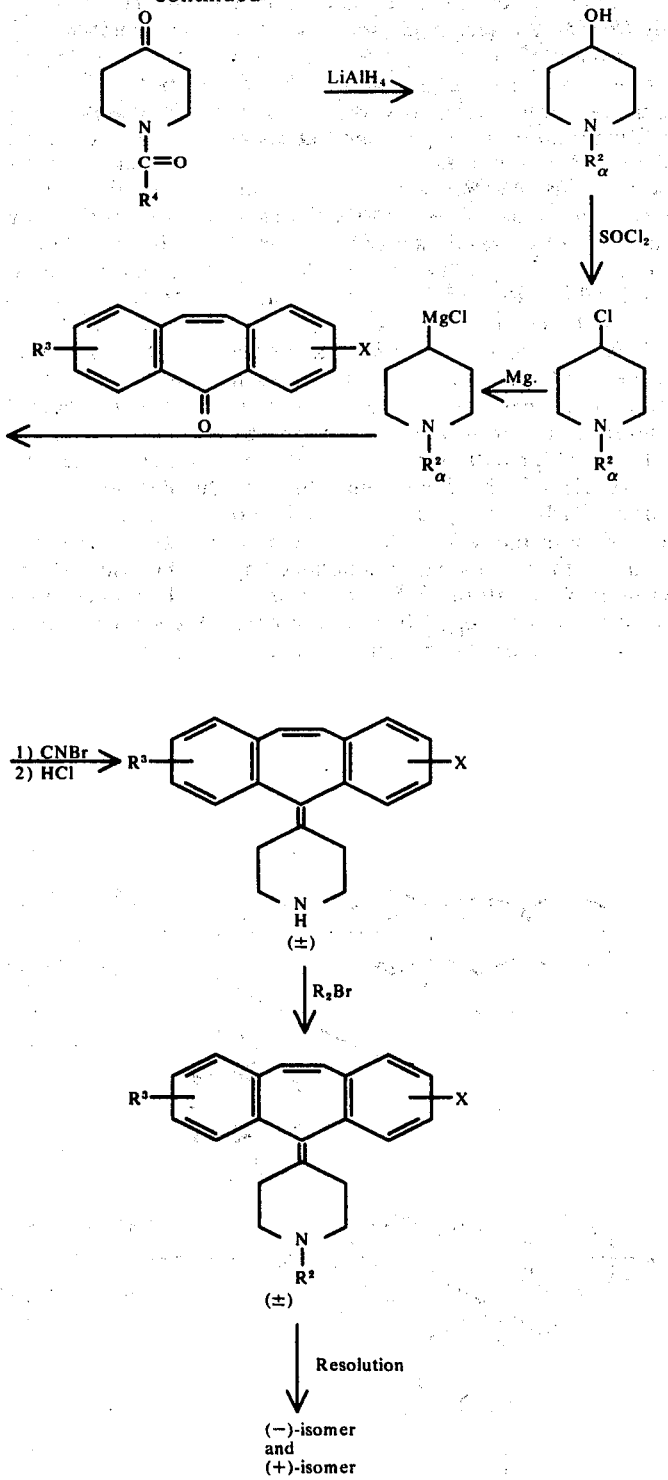

The novel method of treatment of this invention comprises the administration of one of the novel compounds to a psychotic patient. The route of administration can be oral, rectal, intravenous, intramuscular, or subcutaneous. Doses of 0.1 to 20 mg./kg./day and preferably of 0.5 to 10 mg./kg./day of active ingredient are generally adequate, and if preferred it can be administered in divided doses given two to four times daily.

It is to be noted that the precise unit dosage form and dosage level depend upon the requirements of the individual being treated and, consequently, are left to the discretion of the therapist.

Pharmaceutical compositions comprising a novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg., and preferably from 5 to 250 mg.

For anticholinergic purposes the compound, preferably a dextrorotatory form, is administered in capsule, tablet, fluid suspension, or solution form in the amount of b 0.5 to 1000 mgms. per dose taken 2–4 times daily.

EXAMPLE 1

(−)-1-Cyclopropylmethyl-4-(3-trifluoromethylthio-5H-dibenzo-[a,d]cyclohepten-5-ylidene)piperidine Step A: Preparation of 1-cyclopropylmethyl-4-piperidyl-magnesium chloride To an ice-cooled solution of 21.97 g. (0.143 mol) of 4-piperidone hydrochloride hydrate in 80 ml. of water is added dropwise 15.0 g. (0.143 mol) of cyclopropanecarboxylic acid chloride. Simultaneous with the addition of the above acid chloride, 37.53 g. (0.286 mol) of solid potassium carbonate is added in small portions at such a rate that the mixture is basic. When the additions are complete, the solution is stirred 1 hour longer while saturating with solid potassium carbonate. The mixture is extracted with five 100 ml. portions of benzene. The combined benzene phases are dried over magnesium sulfate, filtered, and the benzene removed on a rotary evaporator. The product crystallizes to give 20.78 g. (87%) of 1-(cyclopropanecarbonyl)-4-piperidone, m.p. 69°–72°.

A solution of 20.10 g. (0.120 mol) of 1-(cyclopropanecarbonyl)-4-piperidone in 75 ml. of dry tetrahydrofuran is added dropwise over one hour to a slurry of 9.12 g. (0.240 mol) of lithium aluminum hydride in 100 ml. of dry tetrahydrofuran. The reaction mixture is allowed to warm spontaneously, and then is allowed to stir overnight at room temperature. After cooling the reaction mixture in an ice bath, 40% aqueous sodium hydroxide is added dropwise until a clear, colorless organic phase over a semi-granular, solid aqueous phase is obtained. The organic phase is decanted and the residue is washed with warm tetrahydrofuran. Evaporation of the combined tetrahydrofuran fractions gives 17.81 g. of 1-cyclopropylmethyl-4-piperidinol.

A solution of 16.78 g. (0.141 mol) of thionyl chloride in 160 ml. of benzene is cooled in an ice bath, and while stirring, a solution of 17.55 g. of 1-cyclopropylmethyl-4-piperidinol in 100 ml. of benzene is added dropwise over 30 minutes. The mixture is stirred for 1 hour in the ice bath, 3 hours at room temperature, 2.5 hours at reflux, and overnight at room temperature. The crystalline precipitate is removed by filtration and washed thoroughly with ether. After drying at 65°, there is obtained 19.61 g. (83%) of 1-cyclopropylmethyl-4-chloropiperidine hydrochloride.

A solution of 39.71 g. of 1-cyclopropylmethyl-4-chloropiperidine hydrochloride in 100 ml. of water is cooled in an ice bath and is treated with solid potassium carbonate until the solution is saturated. This mixture is extracted with three 300 ml. portions of ether. The combined ether extracts are dried over magnesium sulfate, filtered, and the ether is removed on a rotary evaporator. The residue if fractionally distilled in vacuo to give 28.64 g. of 1-cyclopropylmethyl-4-chloropiperidine, b.p. 93°–109°/17-18 mm.

Into a flame-dried, nitrogen filled flask equipped with stirrer, condenser, and dropping funnel is placed 4.01 g. (0.165 mol) of magnesium turnings and 20 ml. of tetrahydrofuran. The flask is warmed at 50°-60°, and, while stirring, a solution of 28.64 g. (0.165 mol) of 1-cyclopropylmethyl-4-chloropiperidine in 60 ml. of tetrahydrofuran is added dropwise at such a rate that when the external heating is removed, gentle refluxing occurs. After the Grignard reagent is formed, the mixture is refluxed for one additional hour. Titration of the resulting solution shows it to be 1.20 M 1-cyclopropylmethyl-4-piperidylmagnesium chloride in tetrahydrofuran solution.

Step B: Preparation of 3-amino-5H-dibenzo[a,d]cyclohepten-5-one

3-Bromo-5H-dibenzo[a,d]cyclohepten-5-one (25 g., 0.088 mol), copper turnings (1.14 g., 0.018 mol), cuprous chloride (0.94 g., 0.009 mol), and concentrated aqueous ammonia (50 ml.) are agitated together at 195° in a steel bomb for 24 hours.

The cooled mixture is removed from the vessel, and the large solid mass broken up mechanically and dissolved in warm chloroform (ca. 150 ml.). The aqueous residue from the reaction is extracted once with chloroform, and the combined chloroform fractions are washed with water, dried over sodium sulfate, filtered, and evaporated in vacuo to give 18.9 g. or crude yellow solid.

The crude product is ground in a mortar and recrystallized from ethanol (ca. 200 ml.). The solid obtained is dissolved in warm chloroform, treated with ca. 8 g. of silica gel, filtered, and evaporated in vacuo to give 16 g. of 3-amino-5H-dibenzo[a,d]cyclohepten-5-one.

Following the procedure of Step B, but substituting for the 3-bromo-5H-dibenzo[a,d]cyclohepten-5-one used therein an equimolecular amount of 3-bromo-7-fluoro-5H-dibenzo[a,d]cyclohepten-5-one and 3-bromo-7-methyl-5H-dibenzo[a,d]cyclohepten-5-one, there are produced respectively 3-amino-7-fluoro-5H-dibenzo[a,d]cyclohepten-5-one and 3-amino-7-methyl-5H-dibenzo[a,d]cyclohepten-5-one.

Step C: Preparation of 3-iodo-5H-dibenzo[a,d]cyclohepten-5-one

3-Amino-5H-dibenzo[a,d]cyclohepten-5-one (50 g., 0.226 mol) is slurried in 150 ml. of concentrated hydrochloric acid. Ice (150 ml.) is added, and the stirred mixture cooled in an ice bath and diazotized by dropwise addition of sodium nitrite solution (17 g., 0.248 mol in 80 ml. of water) over 45 minutes. The temperature is held below 5° throughout the addition. The mixture is stirred for an additional 15 minutes and poured slowly into a stirred solution of 160 g. (1 mole) of potassium iodide in 100 ml. of water. The mixture is stirred at room temperature for 1 hour, then stored overnight in the refrigerator.

The resulting slurry is filtered and the filtrate is extracted once with chloroform. The solids are extracted several times with hot chloroform, and the combined chloroform fractions washed with dilute sodium bisulfite and with water, and dried over sodium sulfate. Residual solid from the chloroform extraction is discarded.

The chloroform solution is combined with 100 g. of silica gel, evaporated in vacuo, then stirred with 1:1 chloroform/hexane and added to a column of 1 kg. of silica gel. The column is packed and eluted with 1:1 chloroform hexane. The product fraction, which is eluted after about 3.5 liter of fore-run, is evaporated in vacuo to give 3-iodo-5H-dibenzo[a,d]cyclohepten-5-one (39.7 g., 53%) as a white solid, m.p. 97.5°–99°.

Following the procedure of Step C but substituting for the 3-amino-5H-dibenzo[a,d]cyclohepten-5-one used therein an equimolecular amount of 3-amino-7-fluoro-5H-dibenzo[a,d]cyclohepten-5-one and 3-amino-7-methyl-5H-dibenzo[a,d]cyclohepten-5-one, there are produced respectively, 3-iodo-7-fluoro-5H-dibenzo[a,d]cyclohepten-5-one and 3-iodo-7-methyl-5H-dibenzo[a,d]cyclohepten-5-one.

Step D: Preparation of (±)-1-cyclopropylmethyl-4-(3-iodo-5H-dibenzo[a,d]cyclohepten-5-ylidene) piperidine To an ice-cooled solution of 10.00 g. (0.030 mol) of 3-iodo-5H-dibenzo[a,d]cyclohepten-5-one in 60 ml. of dry tetrahydrofuran is added dropwise 30 ml. of 1.20 M 1-cyclopropylmethyl-4-piperidylmagnesium chloride in tetrahydrofuran. The solution is stirred 2 hours, and then the tetrahydrofuran is removed on a rotary evaporator. The red-oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of hot benzene. The combined benzene extracts are washed with five 200 ml. portions of water, dried over magnesium sulfate, filtered, and the benzene is removed on a rotary evaporator. The residue that remains is placed on a silica gel column packed in chloroform. The column is eluted with chloroform which causes a by-product of the reaction, 3-iodo-5H-dibenzo[a,d]cyclohepten-5-ol, to be eluted. (This by-product may be oxidized to provide the starting material, 3-iodo-5H-dibenzo[a,d]cyclohepten-5-one). When all of the by-product has been eluted, the column is eluted with 1% methanol in chloroform. The eluate is concentrated to give 6.03 g. of an oil which is mainly 1-cyclopropylmethyl-4-(3-iodo-5-hydroxy-5H-dibenzo[a,d]cyclohepten-5-yl)piperidine.

A solution of 4.67 g. of the above oil in 45 ml. of trifluoroacetic acid and 35 ml. of trifluoroacetic anhydride is refluxed for 20 hours. The solution is concentrated on a rotary evaporator and the residue is made basic with 20% sodium hydroxide. The oil that precipitates is extracted into benzene, and this benzene phase is washed with water, dried over magnesium sulfate, filtered, and the benzene removed on a rotary evaporator. The residue, which crystallizes rapidly, is triturated with acetonitrile and collected by filtration. There is obtained 2.58 g. of product, which, when recrystallized from acetonitrile, gives 2.54 g. of (±)-1-cyclopropylmethyl-4-(3-iodo-5H-dibenzo[a,d]cyclohepten-5-ylidene)piperidine, m.p. 139°–141°.

Anal. Calcd. for $C_{24}H_{24}IN$: C, 63.58; H, 5.34; N, 3.09; I, 27.99. Found: C, 63.78; H, 5.57; N, 3.02; I, 28.08.

Similarly prepared is (±)-1-cyclobutylmethyl-4-(3-iodo-5H-dibenzo[a,d]cyclohepten-5-ylidene)piperidine by substituting an equimolecular amount of 1-cyclobutylmethyl-4-piperidylmagnesium chloride for the 1-cyclopropylmethyl-4-piperidylmagnesium chloride.

Following the procedure of Example 1, Step D, but substituting for the 3-iodo-5H-dibenzo[a,d]cyclohepten-5-one used therein an equimolecular amount of 3-iodo-7-methyl-5H-dibenzo[a,d]cyclohepten-5-one or 3-iodo-7-fluoro-5H-dibenzo[a,d]cyclohepten-5-one, there is produced (±)-1-cyclopropylmethyl-4-(3-iodo-7-methyl-5H-dibenzo[a,d]cyclohepten-5-ylidene)-piperidine or (±)-1-cyclopropylmethyl-4-(3-iodo-7-fluoro-5H-dibenzo[a,d]cyclohepten-5-ylidene)piperidine, respectively.

Step E: Resolution of (±)-1-cyclopropylmethyl-4-(3-iodo-5H-dibenzo[a,d]cyclohepten-5-ylidene)piperidine 1. Levorotatory Isomer: To a solution of 11.57 g. (0.0255 mol) of (±)-1-cyclopropylmethyl-4-(3-iodo-5H-dibenzo[a,d]cyclohepten-5-ylidene)piperidine in 245 ml. of hot absolute ethanol is added 9.86 g. (0.0255 mol) of di-p-toluoyl-d-tartaric acid dissolved in 60 ml. of hot absolute ethanol. The solution is stirred and concentrated by boiling to 150 ml. The crystalline precipitate that forms on cooling is removed by filtration, washed with cold absolute ethanol, and dried at 100° in vacuo to give 8.41 g. of material, designated A. The clear ethanol filtrate and washings are designated B.

The 8.41 g. of A is recrystallized from absolute ethanol four times to give a product that has a constant rotation, m.p. 147°–149°; $[\alpha]_{589}^{25} = -128°$; $[\alpha]_{578}^{25} = -136°$, $[\alpha]_{546}^{25} = -161°$, $[\alpha]_{436}^{25} = -369°$, (C = 0.00314 g./ml. pyridine). This material, 3.70 g., is suspended in a small amount of water and is treated with 5% sodium hydroxide solution. The free base that precipitates is extracted into ether, washed with water, and dried over magnesium sulfate. After filtering, the ether is removed on a rotary evaporator. The white solid that remains is dried at 100° to give 1.89 g. of (−)-1-cyclopropylmethyl-4-(3-iodo-5H-dibenzo[a,d]cyclohepten-5-ylidene)-piperidine, m.p. 135°–136.5°; $[\alpha]_{589}^{25} = -141°$, $[\alpha]_{578}^{25} = -150°$, $[\alpha]_{546}^{25} = -180°$, $[\alpha]_{436}^{25} = -431°$, (C = 0.0041 g./10 ml. CHCl$_3$).

2. Dextrorotatory Isomer — The ethanol filtrate and washings, designated B, are concentrated on a rotary evaporator. The residue is treated with 5% sodium hydroxide solution. The free base that precipitates is extracted into chloroform. Evaporation of the chloroform gives 10.09 g. of 1-cyclopropylmethyl-4-(3-iodo-5H-dibenzo[a,d]cyclohepten-5-ylidene)piperidine that is rich in the dextrorotatory isomer. This material is dissolved in 240 ml. of hot absolute ethanol and is treated with 9.02 g. of di-p-toluoyl-l-tartaric acid monohydrate dissolved in 60 ml. of hot absolute ethanol. The solution is stirred and concentrated by boiling to 125 ml. The crystalline precipitate that forms on cooling is removed by filtration, washed with cold absolute ethanol, and dried at 100° in vacuo to give 9.86 g. of material. This material is recrystallized from absolute ethanol three times to give a product that has a constant rotation, m.p. 146°–147°; $[\alpha]_{589}^{25} = +128°$, $[\alpha]_{578}^{25} = +135°$; $[\alpha]_{546}^{25} = +161°$, $[\alpha]_{436}^{25} = +365°$, (C = 0.00309 g./ml. pyridine). This material, 5.29 g., is suspended in a small amount of water and is treated with 5% sodium hydroxide solution. The free base that precipitates is extracted into ether, washed with water, and dried over magnesium sulfate. After filtering, the ether is removed on a rotary evaporator. The white solid that remains is dried at 100° to give. 2.65 g. of (+)-1-cyclopropylmethyl-4-(3-iodo-5H-dibenzo[a,d]cyclohepten-5-ylidene)piperidine, m.p. 135°–136.5°; $[\alpha]_{589}^{25} = +138°$, $[\alpha]_{578}^{25} +147°$, $[\alpha]_{546}^{25} = +176°$, $[\alpha]_{436}^{25} = +422°$, (C - 0.00433 g./ml. CHCl$_3$).

In a similar manner there are produced the (−) and (+) isomers of each of 1-cyclopropylmethyl-4-(3-iodo- 7-methyl-5H-dibenzo[a,d]cyclohepten-5-ylidene)-piperidine and 1-cyclopropylmethyl-4-(3-iodo-7-fluoro-5H-dibenzo[a,d]cyclohepten-5-ylidene)piperidine, and 1-cyclobutylmethyl-4-(3-iodo-5H-dibenzo[a,d]cyclohepten-5-ylidene)piperidine from their respective racemic mixtures.

Step F: Preparation of (−)-cyclopropylmethyl-4-(3-trifluoromethylthio-5H-dibenzo[a,d]cyclohepten-5-ylidene)piperidine A mixture of 2.88 g. (0.0454 mol) of copper dust, 4.32 g. (0.0107 mol) of bis-(trifluoromethylthio)mercury, 1.89 g. (0.00417 mol) of (−)-1-cyclopropylmethyl-4-(3-iodo-5H-dibenzo[a,d]cyclohepten-5-ylidene)-piperidine, and 20 ml. of dimethylformamide is stirred and heated on the steam bath for 6 hours. The mixture is cooled in ice, and 40 ml. of chloroform and 25 ml. of concentrated ammonium hydroxide is added. The mixture is stirred overnight at room temperature and then filtered through a pad of Filter-Cel. The filtrate and chloroform washings are combined and separated from the deep blue aqueous phase. The chloroform phase is washed with water, dried over magnesium sulfate, filtered, and the chloroform is removed on a rotary evaporator. The residue crystallizes rapidly. It is triturated with cold acetonitrile and collected by filtration. This material is recrystallized from acetonitrile to give 1.20 g. (67%) of (−)-1-cyclopropylmethyl-4-(3-trifluoromethylthio-5H-dibenzo[a,d]cyclohepten-5-ylidene)piperidine, m.p. 143°–144°; $[\alpha]_{589}^{25} = -64.1°$, $[\alpha]_{578}^{25} = -68.0°$, $[\alpha]_{546}^{25} = -82.8°$, $[\alpha]_{436}^{25} = -212°$, (C = 0.00513 g./ml. CHCl$_3$).

Anal. Calcd. for $C_{25}H_{24}F_3NS$: C, 70.23; H, 5.66; N, 3.28; F, 13.33. Found: C, 70.40; H, 5.81; N, 3.29, F, 13.04.

Following the procedure of Example 1, Step F, but substituting for the starting material used therein an equimolecular amount of (−)-1-cyclopropylmethyl-4-(3-iodo-7-methyl-5H-dibenzo[a,d]cyclohepten-5-ylidene)piperidine, (−)-1-cyclopropylmethyl-4-(3-iodo-7-fluoro-5H-dibenzo[a,d]cyclohepten-5-ylidene piperidine, or (−)-1-cyclobutylmethyl-4-(3-iodo-5H-dibenzo[a,d]cyclohepten-5-ylidene)piperidine, there are produced respectively (−)-1-cyclopropylmethyl-4-(3-trifluoromethylthio-7-methyl-5H-dibenzo[a,d]cyclohepten-5-ylidene)piperidine, (−)-1-cyclopropylmethyl-4-(3-trifluoromethylthio-7-fluoro-5H-dibenzo[a,d]cyclohepten-5-ylidene)piperidine, and (−)-1-cyclobutylmethyl-4-(3-trifluoromethylthio-5H-dibenzo[a,d]cyclohepten-5-ylidene)piperidine.

EXAMPLE 2

(+)-1-Cyclopropylmethyl-4-(3-trifluoromethylthio-5H-benzo[a,d]cyclohepten-5-ylidene)piperidine A mixture of 4.05 g. (0.0637 mol) of copper dust, 6.05 g. (0.0150 mol) of bis-(trifluoromethylthio)mercury, 2.65 g. (0.00584 mol) of (+)-1-cyclopropylmethyl-4-(3-iodo-5H-dibenzo[a,d]cyclohepten-5-ylidene)-piperidine, and 30 ml. of dimethylformamide is stirred and heated on the steam bath for 6 hours. The mixture is cooled in ice, and 40 ml. of chloroform and 25 ml. of concentrated ammonium hydroxide is added. The mixture is stirred overnight at room temperature and then filtered through a pad of Filter-Cel. The filtrate and chloroform washings are combined and separated from the deep blue aqueous phase. The chloroform phase is washed with water, dried over magnesium sulfate, filtered, and the chloroform is removed on a rotary evaporator. The residue crystallizes rapidly. It is triturated with cold acetonitrile and collected by filtration. This material is recrystallized from acetonitrile to give 1.37 g. (55%) of (+)-1-cyclopropylmethyl-4-(3-trifluoromethylthio-5H-dibenzo[a,d]cyclohepten-5-ylidene)piperidine, m.p. 143°–144°; $[\alpha]_{589}^{25} = +64.2°$; $[\alpha]_{578}^{25} = +68.9°$; $[\alpha]_{546}^{25} = +83.5°$; $[\alpha]_{436}^{25} = +213°$ (c) = 0.00515 g./ml. CHCl$_3$.

Anal. Calcd. for $C_{25}H_{24}F_3NS$: C, 70.23; H, 5.66; N, 3.28; F, 13.33. Found: C, 70.85; H, 5.78; N, 3.33; F, 13.55.

Following the procedure of Example 2, but substituting for the starting material used therein an equimolar amount of (+)-1-cyclopropylmethyl-4-(3-iodo-7-methyl-5-H-dibenzo[a,d]cyclohepten-5-ylidene)piperidine, (+)-1-cyclopropylmethyl-4-(3-iodo-7-fluoro-5H-dibenzo[a,d]cyclohepten-5-ylidene)piperidine or (+)-1-cyclobutylmethyl-4-(3-iodo-5H-dibenzo[a,d]cyclohepten-5-ylidene)piperidine, there are produced respectively (+)-1-cyclopropylmethyl-4-(3-trifluoromethylthio-7-methyl-5H-dibenzo[a,d]cyclohepten-5-ylidene)piperidine, (+)-1-cyclopropylmethyl-4-(3-trifluoromethylthio-7-fluoro-5H-dibenzo[a,d]cyclohepten-5-ylidene)piperidine and (+)-1-cyclobutylmethyl-4-(3-trifluoromethylthio-5H-dibenzo[a,d]cyclohepten-5-ylidene)piperidine.

EXAMPLE 3

(±)-1-Cyclopropylmethyl-4-(3-trifluoromethylthio-5H-dibenzo[a,d]cyclohepten-5-ylidene)piperidine Step A: Preparation of 3-trifluoromethylthio-5H-dibenzo[a,d]cyclohepten-5-one A mixture of 42.56 g. of bis(trifluoromethylthio)mercury, 17.27 g. of 3-bromo-5H-dibenzo[a,d]cyclohepten-5-one, 28 g. of electrolytic copper dust, 98 ml. of quinoline and 84 ml. of pyridine is stirred and heated from 100° to 195° C. for 18 hours. The mixture is shaken with 400 ml. of 6 N hydrochloric acid and 400 ml. benzene. The organic phase is washed with 5 × 300 ml. of 3 N hydrochloric acid and 5 × 300 ml. of water, dried over magnesium sulfate, filtered and concentrated to dryness. The crystalline residue is recrystallized from 100 ml. of methanol to give 14.83 g. (78%) of 3-trifluoromethylthio-5H-dibenzo[a,d]cyclohepten-5-one, m.p. 87°–88° C.

Following the procedure of Example 3, Step A, but substituting for the starting material used therein an equimolar amount of 3-bromo-7-methyl-5H-dibenzo[a,d]cyclohepten-5-one and 3-bromo-7-fluoro-5H-dibenzo[a,d]cyclohepten-5-one, there are produced respectively 3-trifluoromethylthio-7-methyl(and 7-fluoro)-5H-dibenzo[a,d]cyclohepten-5-one.

Step B: Preparation of (±)-1-cyclopropylmethyl-4-(3-trifluoromethylthio-5H-dibenzo[a,d]cyclohepten-5-ylidene)piperidine To an ice-cooled solution of 10.0 g. (0.0326 mol) of 3-trifluoromethylthio-5H-dibenzo[a,d]cyclohepten-5-one in 60 ml. of dry tetrahydrofuran is added dropwise 29 ml. of 1.14 M 1-cyclopropylmethyl-4-piperidylmagnesium chloride in tetrahydrofuran. The solution is stirred for 2 hours while being allowed to warm to room temperature, and then the tetrahydrofuran is removed on a rotary evaporator. The red-oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of hot benzene. The combined benzene extracts are washed with four 150 ml. portions of water, dried over magnesium sulfate, filtered, and the benzene is removed on a rotary evaporator. The remaining residue is placed on a silica gel column packed in chloroform. The column is eluted with chloroform which causes a by-product of the reaction, 3-trifluoromethylthio-5H-dibenzo[a,d]cyclohepten-5-ol, to be eluted. (This by-product may be oxidized to provide the starting material, 3-trifluoromethylthio-5H-dibenzo[a,d]cyclohepten-5-one). When all of the by-product has been eluted, the column is eluted with 2% methanol in chloroform. The eluate is concentrated to give 7.0 g. of an oil which is mainly 1-cyclopropylmethyl-4-(3-trifluoromethylthio-5-hydroxy-5H-dibenzo[a,d]cyclohepten-5-yl)piperidine.

A solution of 7.0 g. of the above oil in 40 ml. of trifluoroacetic acid and 50 ml. of trifluoroacetic anhydride is refluxed overnight. The solution is concentrated on a rotary evaporator and the residue is made basic with sodium hydroxide solution. The oil that precipitates is extracted into ether, and this ether phase is washed with water, dried over magnesium sulfate, filtered, and the ether removed on a rotary evaporator. The residue, which crystallizes rapidly, is triturated with acetonitrile and collected by filtration. The material is recrystallized from acetonitrile, collected, and dried at 100° to give 4.26 g. of (±)-1-cyclopropylmethyl-4-(3-trifluoromethylthio-5H-dibenzo[a,d]cyclohepten-5-ylidene)piperidine, m.p. 122°–123°.

Anal. Calcd. for $C_{25}H_{24}F_3NS$: C, 70.23; H, 5.66; N, 3.28, S, 7.50. Found: C, 70.07; H, 5.31; N, 3.04; S, 7.38.

Following the procedure of Example 3, Step B, but substituting for the 3-trifluoromethylthio-5H-dibenzo[a,d]cyclohepten-5-one used therein, an equimolecular amount of 7-fluoro(and 7-methyl)-3-trifluoromethylthio-5H-dibenzo[a,d]cyclohepten-5-one respectively, there is produced (±)-1-cyclopropylmethyl-4-(7-fluoro-3-trifluoromethyl-5H-dibenzo[a,d]cyclohepten-5-ylidene)piperidine and (±)-1-cyclopropylmethyl-4-(7-methyl-3-trifluoromethylthio-5H-dibenzo[a,d]cyclohepten-5-ylidene)piperidine.

Following the procedure substantially as described in Example 3, Step B, but substituting for the 1-cyclopropylmethyl-4-piperidylmagnesium chloride used therein, an equimolecular amount of 1-methyl-4-piperidylmagnesium chloride, there is produced (±)-1-methyl-4-(3-trifluoromethylthio-5H-dibenzo[a,d]cyclohepten-5-ylidene)piperidine, m.p. 115°–116.5° C.

EXAMPLE 4

(±)-1-Cyclopropylmethyl-4-(3-trifluoromethylsulfonyl-5H-dibenzo[a,d]cyclohepten-5-ylidene)piperidine Step A: Preparation of 3-trifluoromethylsulfonyl-5H-dibenzo[a,d]cyclohepten-5-one A solution of 6.00 g. of 3-trifluoromethylthio-5H-dibenzo[a,d]cyclohepten-5-one in 240 ml. of acetic acid at 17°–18° C. is treated dropwise with 54 ml. of 30% hydrogen peroxide with stirring. The mixture is stirred at room temperature for 192 hours. The mixture is poured into 1.5 liters of water and extracted with five 125 ml. portions of chloroform. The combined chloroform extracts are washed with 4 × 200 ml. of water and 200 ml. of saturated sodium carbonate and 3 × 200 ml. of water. The chloroform is dried over magnesium sulfate, filtered, and evaporated to dryness. The residue is triturated with ethanol. The solids are collected on a filter and dried to give 3.90 g. of crude product. This material is chromatographed on a silica gel (300 g.) column by elution with benzene. The appropriate fractions were combined and concentrated to dryness to give 2.5 g. of 3-trifluoromethylsulfonyl-5H-dibenzo[a,d]cyclohepten-5-one, m.p. 145°–149° C.

Step B: Preparation of (±)-1-cyclopropylmethyl-4-(3-trifluoromethylsulfonyl-5H-dibenzo[a,d]cyclohepten-5-ylidene)piperidine Employing the procedure substantially as described in Example 3, Step B, but substituting for the 3-trifluoromethylthio-5H-dibenzo[a,d]cyclohepten-5-one used therein an equimolecular amount of 3-trifluoromethylsulfonyl-5H-dibenzo[a,d]cyclohepten-5-one, there is produced 8±)-1-cyclopropylmethyl-4-(3-trifluoromethylsulfonyl-5H-dibenzo[a,d]cyclohepten-5-ylidene)piperidine, m. p. 125°–127° C.

Following the procedure substantially as described in Example 4, Step B, but substituting for the 1-cyclopropylmethyl-4-piperidylmagnesium chloride used therein an equimolecular amount of 1-cyclobutylmethyl-4-piperidylmagnesium chloride, there is produced (±)-1-cyclobutylmethyl-4-(3-trifluoromethylsulfonyl-5H-dibenzo[a,d]cyclohepten-5-ylidene)piperidine, m.p. 101°–106° C.

Following the procedure of Example 4 but substituting for the 3-trifluoromethylthio-5H-dibenzo[a,d]cyclohepten-5-one used in Step A thereof, an equimolecular amount of 3-trifluoromethylthio-7-methyl (and 7-fluoro)dibenzo[a,d]cyclohepten-5-one followed by treatment of the products with 1-cyclopropylmethyl-4-piperidylmagnesium chloride, there is produced respectively (±)-1-cyclopropylmethyl-4-(3-trifluoromethylsulfonyl-7-methyl-5H-dibenzo[a,d]cyclohepten-5-ylidene)piperidine and (±)-1-cyclopropylmethyl-4-(3-trifluoromethylsulfonyl-7-fluoro-5H-dibenzo[a,d]cyclohepten-5-ylidene)piperidine.

EXAMPLE 5

(±)-1-Cyclobutylmethyl-4-(3-trifluoromethylthio-5H-dibenzo[a,d]cyclohepten-5-ylidene)piperidine Step A: Preparation of 1-cyclobutylmethyl-4-piperidylmagnesium chloride Employing the procedure substantially as described in Example 1, Step A, but substituting for the cyclopropanecarboxylic acid chloride used therein, an equimolecular amount of cyclobutanecarboxylic acid chloride, there is produced a tetrahydrofuran solution of 1-cyclobutylmethyl-4-piperidylmagnesium chloride.

Step B: Preparation of (±)-1-Cyclobutylmenthyl-4-(3-trifluromenthylthio-5H-dibenzo[a,d]cyclohepten-5-ylidene)piperidine Employing the procedure of Example 3, Step B, but substituting for the 1-cyclopropylmethyl-4-piperidylmagnesium chloride used therein, an equivalent amount of 1-cyclobutylmethyl-4-piperidylmagnesium chloride, there is produced (±)-1-cyclobutylmethyl-4-(3-trifluoromethylthio-5-H-dibenzo[a,d]cyclohepten-5-ylidene)piperidine, m.p. 114.5°–116° C. after recrystallization from acetonitrile.

EXAMPLE 6

(±)-1-Cyclobutylmethyl-4-(3-trifluoromethylsulfonyl-5-H-dibenzo[a,d]cyclohepten-5-ylidene)piperidine Following the procedure substantially as described in Example 4, Step B, but substituting for the 1-cyclopropylmethyl-4-piperidylmagnesium chloride, an equimolecular amount of 1-cyclobutylmethyl-4-piperidylmagnesium chloride, there is produced (±)-1-cyclobutylmethyl-4-(3-trifluoromethylsulfonyl-5H-dibenzo[a,d]cyclohepten-5-ylidene)piperidine, m.p. 126°–128° C.

EXAMPLE 7

(±)-1-Methylenecyclopropylmethyl-4-(3-trifluoromethylthio-5H-dibenzo[a,d]cyclohepten-5-ylidene)piperidine Step A: Preparation of 4-(3-trifluoromethylthio-5H-dibenzo[a,d]cyclohepten-5-ylidene)piperidine A solution of 3.78 g. of 1-methyl-4-(3-trifluoromethylthio-5H-dibenzo[a,d]cyclohepten-5-ylidene)piperidine in 35 ml. of benzene is added dropwise over 45 minutes to a stirred solution of 1.3 g. of cyanogen bromide in 35 ml. of benzene. After stirring at room temperature overnight the solution is evaporated to dryness and coevaporated with acetonitrile.

To the oily residue is added 100 ml. of acetic acid, 12 ml. of concentrated hydrochloric acid, and 50 ml. of water. This mixture is refluxed for 16 hours. The mixture is concentrated to dryness in vacuo. The residue is dissolved in chloroform and made basic by addition of sodium bicarbonate solution. The aqueous phase is extracted well with chloroform and the combined organic layers are washed with water, dried and filtered. The filtrate is concentrated to dryness in vacuo to give 3.73 g. of 4-(3-trifluoromethylthio-5H-dibenzo[a,d]cyclohepten-5-ylidene)piperidine, m.p. 151.5°–154.5° C.

Step B: Preparation of (±)-1-methylenecyclopropylmethyl-(±)-4-(3-trifluoromethylthio-5H-dibenzo[a,d]cyclohepten-5-ylidene)piperidine A mixture of 2 g. of the product from Step A, 0.5 g. of sodium bicarbonate and 0.778 g. of (±)-methylenecyclopropylmethylbromide in 60 ml. of absolute ethanol is refluxed overnight. An additional amount of 0.132 g. of the bromide is added and refluxing is continued for 6 more hours when another 0.132 g. of bromide is added followed by refluxing overnight. The cooled mixture is filtered and the filtrate is concentrated to dryness in vacuo. The residue is partitioned between water and chloroform. The separated water phase is extracted again with chloroform. The combined chloroform extracts are washed with water, dried over magnesium sulfate and concentrated to dryness. Recrystallization of the residue from acetonitrile gives (±)-1-methylenecyclopropylmethyl-(±)-4-(3-trifluoromethylthio-5H-dibenzo[a,d]cyclohepten-5-ylidene)piperidine, m.p. 86°–89° C.

Employing the procedure substantially as described in Example 7, Step B, but substituting for the (±)-methylenecyclopropylmethyl bromide used therein, an equimolecular amount of (−)-methylenecyclopropylmenthyl bromide, there is produced (−)-1-methylenecyclopropylmethyl-(±)-4-(3-trifluromethylthio-5H-dibenzo[a,d]cyclohepten-5-ylidene)piperidine, m.p. 91°–93° C.

Employing the procedure substantially as described in Example 7, Step B, but substituting for the methylenecyclopropyl bromide used therein, an equimolecular amount of cyclopropylmethyl bromide, cyclobutylmethyl, and ethylenebromohydrin, there are produced respectively:

(±)-1-cyclopropylmethyl-4-(3-trifluoromethylthio-5H-dibenzo[a,d]cyclohepten-5-ylidene)piperidine;

(±)-1-cyclobutylmethyl-4-(3-trifluoromethylthio-5H-dibenzo[a,d]cyclohepten-5-ylidene)piperidine, and (±)-1-hydroxyethyl-4-(3-trifluoromethylthio-5H-dibenzo[a,d]cyclohepten-5-ylidene)piperidine.

EXAMPLE 8

(±)-1-Methylenecyclopropylmethyl-4-(3-trifluoromethylsulfonyl-5H-dibenzo[a,d]cyclohepten-5-ylidene)-piperidine Employing the procedure substantially as described in Example 7 but substituting for the 3-trifluoromethylthio compound used in Step A thereof an equimolecular amount of the corresponding 3-trifluoromethylsulfonyl compound, there is produced:

(±)-4-(3-trifluoromethylsulfonyl-5H-dibenzo[a,d-]cyclohepten-5-ylidene)piperidine, m.p. 189.5°–192.5;°;

which upon treatment with (−)-methylenecyclopropylmethyl bromide, cyclopropylmethyl bromide, cyclobutylmethyl bromide or ethylene bromohydrin in accordance with Example 7, Step B, produces respectively:

(±)-1-methylenecyclopropylmethyl-(±)-4-(3-trifluoromethylsulfonyl-5H-dibenzo[a,d]cyclohepten-5-ylidene)piperidine, m.p. 132°–141° C.;

(±)-1-cyclopropylmethyl-4-(3-trifluoromethylsulfonyl-5H-dibenzo[a,d]cyclohepten-5-ylidene)piperidine;

(±)-1-cyclobutylmethyl-4-(3-trifluoromethylsulfonyl-5H-dibenzo[a,d]cyclohepten-5-ylidene)piperidine, or (±)-1-hydroxyethyl-4-(3-trifluoromethylsulfonyl-5H-dibenzo[a,d]cyclohepten-5-ylidene)piperidine.

EXAMPLE 9

(±)-1-Hydroxyethyl-4-(3-trifluoromethylsulfonyl5H-dibenzo[a,d]cyclohepten-5-ylidene)piperidine A solution of 0.244 g. of ethylene oxide of 30 ml. of methanol at dry-ice temperature is added to an ice cold solution of 2.55 g. of 4-(3-trifluoromethylsulfonyl-5H-dibenzo[a,d]cyclohepten-5-ylidene)piperidine in 15 ml. of chloroform and 75 ml. of methanol. The solution is stirred at ambient temperature overnight. A second quantity (0.25 g.) of ethylene oxide is added as before and the mixture is again stirred overnight. The mixture is concentrated to dryness and the residue is coevaporated in vacuo several times with acetonitrile. The product is recrystallized several times from acetonitrile to give (±)-1-hydroxyethyl-4-(3-trifluoromethylsulfonyl-5H-dibenzo[a,d]cyclohepten-5-ylidene)-piperidine, m.p. 141°–144° C.

Employing the procedure substantially as described in Example 9 but substituting for the trifluoromethylsulfonyl compound used therein, an equimolecular amount of the corresponding trifluoromethylthio compound, there is produced (±)-1-hydroxyethyl-4-(3-trifluoromethylthio-5H-dibenzo[a,d]cyclohepten-5-ylidene)piperidine, m.p. 116°–118° C., clearing at 127° C.

EXAMPLE 10

(±) and
(−)-1-Hydroxyethyl-4-(3-trifluoromethylthio-5H-dibenzo[a,d]cyclohepten-5-ylidene)piperidine Step A: Preparation of (±)-4-(3-iodo-5H-dibenzo[a,d]cyclohepten-5-ylidene)piperidine Following the procedure of Example 7, Step A, but substituting for the (±)-1-methyl-4-(3-trifluoromethylthio-5H-dibenzo[a,d]cyclohepten-5-ylidene) piperidine used therein an equimolecular amount of (±)-1-cyclopropylmethyl-4-(3-iodo-5H-dibenzo[a,d]cyclohepten-5-ylidene)piperidine, there is produced (±)-4-(3-iodo-5H-dibenzo[a,d]cyclohepten-5-ylidene)piperidine.

Step B: Preparation of (±)-1-hydroxyethyl-4-(3-iodo-5H-dibenzo[a,d]cyclohepten-5-ylidene)piperidine Following the procedure substantially as described in Example 9 but substituting for (±)-4-(3-trifluoromethysulfonyl-5H-dibenzo[a,d]cyclohepten-5-ylidene)piperidine, and equimolecular amount of (±)-4-(3-iodo-5H-dibenzo[a,d]cyclohepten-5-ylidene)piperidine, there is produced (±)1-hydroxyethyl-4-(3-iodo-5H-dibenzo[a,d]cyclohepten-5-ylidene)piperidine.

Step C: Preparation of (±) and (−)-1-hydroxyethyl-4-(3-iodo-5H-dibenzo[a,d]cyclohepten-5-ylidene)piperidine Following the procedure of Example 1, Step E, for the resolution of the optical isomers but substituting for the racemic mixture used therein, an equimolecular amount of the racemate from Step B of this example, there is produced (±) and (−)-1-hydroxyethyl-4-(3-iodo-5H-dibenzo[a,d]cyclohepten-5-ylidene)piperidine.

Step D: Preparation of (±) and (−)-1-hydroxyethyl-4-(3-trifluoromethylthio-5H-dibenzo[a,d]cyclohepten-5-ylidene)piperidine Following the procedure substantially as described in Example 1 Step F, but substituting for the (−)-1-cyclopropylmethyl-4-(3-iodo-5H-dibenzo[a,d]cyclohepten-5-ylidene)piperidine used therein, an equimolecular amount of the (±) and (−)-1-hydroxyethyl-4-(3-iodo-5H-dibenzo[a,d]cyclohepten-5-ylidene)piperidine respectively, there is produced (±)-1-hydroxyethyl-4-(3-trifluoromethylthio-5H-dibenzo[a,d]cyclohepten-5-ylidene)piperidine and (31)-1-hydroxyethyl-4-(3-trifluoromethylthio-5H-dibenzo[a,d]cyclohepten-4-ylidene)piperidine.

EXAMPLE 11

(±)-1-Methylenecyclopropylmethyl-(±) and (−)-4-(3-trifluoromethylthio-5H-dibenzo[a,d]cyclohepten-5-ylidene)piperidine Step A: Preparation of (±)-1-methylenecyclopropylmethyl-(±)-4-(3-iodo-5H-dibenzo[a,d]cyclohepten-5-ylidene)piperidine Following the procedure of Example 7, Step B, but substituting for the 4-(3-trifluoromethylthio-5H-dibenzo[a,d]cyclohepten-5-ylidene)piperidine used therein, an equimolecular amount of (±)-4-(3-iodo-5H-dibenzo[a,d]cyclohepten-5-ylidene)piperidine, there is produced (±)-1-methylenecyclopropylmethyl-(±)-4-(3-iodo-5H-dibenzo[a,d]cyclohepten-5-ylidene)piperidine.

Step B: Preparation of (±)-1-methylenecyclopropylmethyl-(±) and (−)-4-(3-iodo-5H-dibenzo[a,d]cyclohepten-5-ylidene)piperidine Following the procedure of Example 1, Step E, for the resolution of the optical isomers but substituting for the racemic mixture used therein an equimolecular amount of the racemate from Step A of this example, there is produced (±)-1-methylenecyclopropylmethyl-(±) and (−)-4-(3-iodo-5H-dibenzo[a,d]cyclohepten-5-ylidene)piperidine.

Step C: Preparation of (±)-1-methylenecyclopropylmethyl-(±) and (−)-4-(3-trifluoromethylthio-5H-dibenzo[a,d]cyclohepten-5-ylidene)piperidine Following the procedure substantially as described in Example 1, Step F, but substituting for the (−)-1-cyclopropylmethyl-4-(3-iodo-5H-dibenzo[a,d]cyclohepten-5-ylidene)piperidine used therein an equimolecular amount of (±)-1-methylenecyclopropylmethyl-(+) and (−)-4-(3-iodo-5H-dibenzo[a,d]cyclohepten-5-ylidene)piperidine respectively, there is produced:

(±)-1-methylenecyclopropylmethyl-(±)-4-(3-trifluoromethylthio-5H-dibenzo[a,d]cyclohepten-5-ylidene)piperidine and (±)-1-methylenecyclopropylmethyl-(−)-4-(3-trifluoromethylthio-5H-dibenzo[a,d]cyclohepten-5-ylidene)piperidine

EXAMPLE 12

Pharmaceutical Compositions

A typical tablet containing 100 mg. of (−)-1-cyclopropylmethyl-4-(3-trifluoromethylthio-5H-dibenzo[a,d]cyclohepten-5-ylidene)piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets.

Tablet Formula

| Ingredient | Mg. per Tablet |
| --- | --- |
| (−)-1-cyclopropylmethyl-4-(3-trifluoromethylthio-5H-dibenzo[a,d]cyclohepten-5-ylidene)piperidine | 100 mg. |
| Calcium phosphate | 52 mg. |
| Lactose | 60 mg. |
| Starch | 10 mg. |
| Magnesium stearate | 1 mg. |

Similarly prepared are tablets comprising as active ingredient any of the antipsychotic compounds described herein.

What is claimed is:
1. A compound of structural formula:

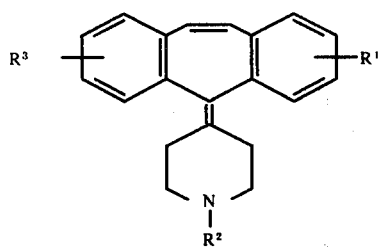

or a pharmaceutically acceptable salt thereof, wherein
$R^1$ is —$SCF_3$ or $SO_2CF_3$,
$R^2$ is

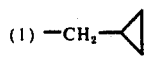

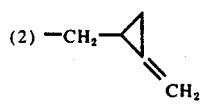

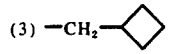

(4) —$CH_2CH_2OH$;

and
$R^3$ is hydrogen, $C_{1-3}$ alkyl or fluoro.

2. The compound of claim 1 of structural formula:

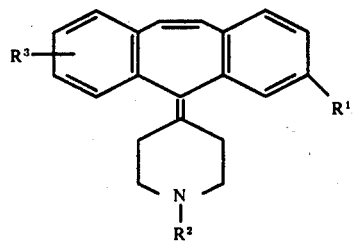

or pharmaceutically acceptable salt thereof.

3. The compound of claim 2 or pharmaceutically acceptable salt thereof wherein $R^3$ is hydrogen.

4. The compound of claim 3 or pharmaceutically acceptable salt thereof wherein $R^1$ is —$SCF_3$.

5. The compound of claim 3 or pharmaceutically acceptable salt thereof wherein $R^1$ is —$SO_2CF_3$.

6. The compound of claim 4, which is 1-cyclopropylmethyl-4-(3-trifluoromethylthio-5H-dibenzo[a,d]cyclohepten-5-ylidene)piperidine, or pharmaceutically acceptable salt thereof.

7. The levorotatory enantiomer of the compound of claim 6 which is (—)-1-cyclopropylmethyl-4-(3-trifluoromethylthio-5H-dibenzo[a,d]cyclohepten-5-ylidene)piperidine, or pharmaceutically acceptable salt thereof.

8. The dextrorotatory enantiomer of the compound of claim 6, which is (±)-1-cyclopropylmethyl-4-(3-trifluoromethylthio-5H-dibenzo[a,d]cyclohepten-5-ylidene)piperidine, or pharmaceutically acceptable salt thereof.

9. A levorotatory enantiomer of the compound of structural formula:

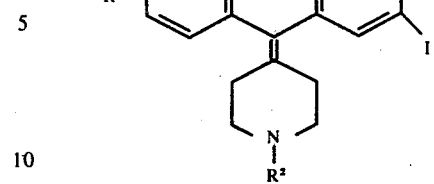

wherein
$R^2$ is

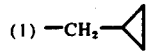

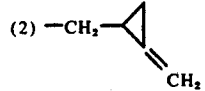

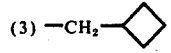

(4) —$CH_2CH_2OH$;

and
$R^3$ is hydrogen, $C_{1-3}$ alkyl or fluoro.

10. The levorotatory enantiomer of the compound of claim 9 of structural formula:

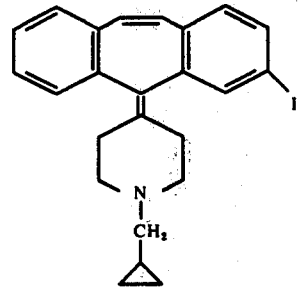

11. A method of treating psychoses which comprises the administration to a patient in need of such treatment an effective amount of a compound of structural formula:

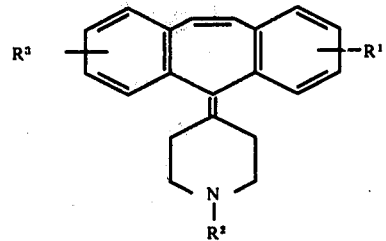

or pharmaceutically acceptable salt thereof, wherein
$R^1$ is —$SCF_3$ or $SO_2CF_3$;
$R^2$ is

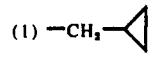

-continued (2) 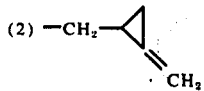

(3) 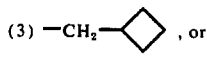, or (4) —CH$_2$CH$_2$OH;

and

R$^3$ is hydrogen, C$_{1-3}$ alkyl or fluoro.

12. The method of claim 11 wherein the compound is the levorotatory enantiomer of the compound of structural formula:

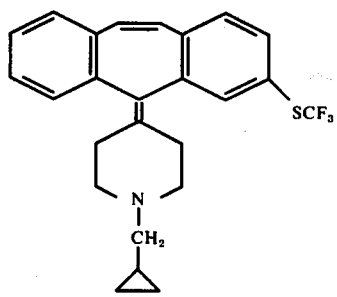

or pharmaceutically acceptable salt thereof.

13. A pharmaceutical composition in unit dosage form for the treatment of psychoses comprising a carrier and an effective amount of a compound of structural formula:

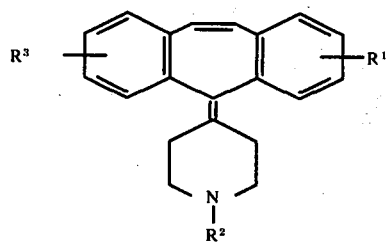

or a pharmaceutically acceptable salt thereof, wherein
R$^1$ is —SCF$_3$ or SO$_2$CF$_3$,
R$^2$ is (1) —CH$_2$—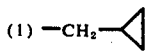

(2) 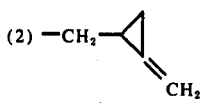

(3) 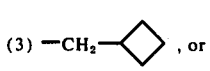, or (4) —CH$_2$CH$_2$OH;

and

R$^3$ is hydrogen, C$_{1-3}$ alkyl or fluoro.

14. The pharmaceutical composition of claim 13, wherein the compound is the levorotatory enantiomer of the compound of structural formula:

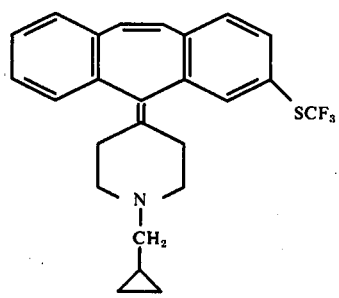

or pharmaceutically acceptable salt thereof.

15. The dextrorotatory enantiomer of the compound of claim 9 of structural formula:

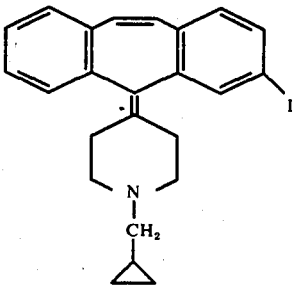

* * * * *